US012180135B2

(12) United States Patent
Knauf et al.

(10) Patent No.: US 12,180,135 B2
(45) Date of Patent: Dec. 31, 2024

(54) PROCESS FOR THE CONTINUOUS PRODUCTION OF NITROBENZENE

(71) Applicants: Covestro Deutschland AG, Leverkusen (DE); Covestro Intellectual Property GmbH & Co. KG, Leverkusen (DE)

(72) Inventors: Thomas Knauf, Dormagen (DE); Murat Kalem, Neuss (DE); Christian Drumm, Frohnhofen (DE); Alexandre Racoes, Krefeld (DE)

(73) Assignee: Covestro Deutschland AG, Leverkusen (DE)

( * ) Notice: Subject to any disclaimer, the term of this patent is extended or adjusted under 35 U.S.C. 154(b) by 521 days.

(21) Appl. No.: 17/602,366

(22) PCT Filed: Apr. 14, 2020

(86) PCT No.: PCT/EP2020/060436
§ 371 (c)(1),
(2) Date: Oct. 8, 2021

(87) PCT Pub. No.: WO2020/212333
PCT Pub. Date: Oct. 22, 2020

(65) Prior Publication Data
US 2022/0169592 A1     Jun. 2, 2022

(30) Foreign Application Priority Data

Apr. 17, 2019 (EP) ..................... 19169873
Mar. 23, 2020 (EP) ..................... 20164914

(51) Int. Cl.
C07C 201/08     (2006.01)
B01D 17/02     (2006.01)
(Continued)

(52) U.S. Cl.
CPC ............ *C07C 201/08* (2013.01); *B01D 17/02* (2013.01); *B01D 19/0057* (2013.01);
(Continued)

(58) Field of Classification Search
CPC ........................ C07C 201/08; C07C 205/06
See application file for complete search history.

(56) References Cited

U.S. PATENT DOCUMENTS 3,092,671 A    6/1963  Humphrey et al.
3,771,654 A *  11/1973 Meissner ............. B01D 17/041
                                              210/322
(Continued)

FOREIGN PATENT DOCUMENTS

CN     109320423 A    2/2019
DE   102009005324 A1  7/2010

OTHER PUBLICATIONS

Stewart, Maurice et al., Gulf Equipment Guides, Gas-Liquid and Liquid-Liquid Separators, chapters 3.3 to 3.5, 2009.
(Continued)

*Primary Examiner* — Jafar F Parsa
(74) *Attorney, Agent, or Firm* — Donald R. Palladino

(57) ABSTRACT

The invention relates to a continuously operating process for producing nitrobenzene, comprising the following steps: a) nitriding benzene in adiabatic conditions with sulfuric acid and nitric acid, using a stoichiometric excess of benzene in relation to the nitric acid; b) first separating a gaseous phase containing benzene and gaseous secondary components from the raw process product of the nitridation in a gas separator provided specifically for this purpose, then separating, in a downstream phase-separating apparatus, the resulting liquid phase, which is depleted in gaseous components and contains nitrobenzene and sulfuric acid, into a sulfuric acid phase and a nitrobenzene phase; and c) pro-
(Continued)

cessing the nitrobenzene phase, obtaining nitrobenzene. The invention also relates to a production plant suitable for carrying out the claimed process.

16 Claims, 6 Drawing Sheets

(51) Int. Cl.
  *B01D 19/00* (2006.01)
  *B01J 19/24* (2006.01)
  *C07C 201/16* (2006.01)
(52) U.S. Cl.
  CPC ......... *B01J 19/2425* (2013.01); *C07C 201/16* (2013.01); *B01J 2219/00033* (2013.01)

(56) References Cited

U.S. PATENT DOCUMENTS

| | | |
|---|---|---|
| 5,963,878 A | 10/1999 | Brereton et al. |
| 6,288,289 B1 | 9/2001 | Boyd et al. |
| 7,344,650 B2 | 3/2008 | Knauf et al. |
| 8,357,827 B2 | 1/2013 | Muennig et al. |
| 9,227,909 B2 | 1/2016 | Knauf et al. |
| 9,284,256 B2 | 3/2016 | Knauf et al. |
| 2003/0055300 A1 | 3/2003 | Chrisochoou et al. |
| 2010/0076230 A1 | 3/2010 | Knauf et al. |
| 2011/0196177 A1* | 8/2011 | Munnig ................ C07C 201/08 568/939 |
| 2013/0204043 A1 | 8/2013 | Knauf et al. |
| 2015/0175521 A1 | 6/2015 | Knauf et al. |
| 2017/0152210 A1* | 6/2017 | Knauf ................... C07C 201/08 |

OTHER PUBLICATIONS

Kidnay, Arthur J. et al., Fundamentals of Natural Gas Processing, chapter 5, pp. 105 to 117, 2011.
Manning, Francis S. et al., Oilfield Processing, Crude Oil, vol. 2, chapter 6, pp. 79 to 112, 1995.
International Search Report, PCT/EP2020/060436, date of mailing: Jul. 14, 2020, Authorized officer: Irmgard Seitner.

* cited by examiner

PROCESS FOR THE CONTINUOUS PRODUCTION OF NITROBENZENE

CROSS-REFERENCE TO RELATED APPLICATION

This application is a national stage application under 35 U.S.C. § 371 of PCT/EP2020/060436, filed Apr. 14, 2020, which claims the benefit of European Application No. 19169873.7, filed Apr. 17, 2019 and European Application No. 20164914.2, filed Mar. 23, 2020, each of which is incorporated herein by reference.

FIELD

The invention relates to a continuously operated process for the preparation of nitrobenzene, comprising the steps of: a) nitrating benzene under adiabatic conditions with sulfuric acid and nitric acid using a, based on nitric acid, stoichiometric excess of benzene; b) first removing a gaseous phase comprising benzene and gaseous secondary components from the crude process product of the nitration in a gas separator provided specifically for this purpose, followed by separating the liquid phase thus obtained comprising nitrobenzene and sulfuric acid and depleted of gaseous constituents in a downstream phase separation apparatus into a sulfuric acid phase and a nitrobenzene phase; c) working up the nitrobenzene phase to obtain nitrobenzene.

The invention also relates to a production plant suitable for performing the process according to the invention.

BACKGROUND

The nitration of benzene with nitric acid in the presence of sulfuric acid to give nitrobenzene and water has already been the subject of numerous publications and patent applications. A distinction is made here between two basic types of processes, the "isothermal" mode and the "adiabatic" mode.

In the isothermal mode, the (considerable) heat of reaction from the nitration is removed as far as possible by indirect cooling using a heat transfer medium. An isothermal process for preparing nitrobenzene, in which a reaction loop is used, is described in U.S. Pat. No. 3,092,671 B1. In this process—see FIG. 1 and the explanatory passages of text—benzene and a mixture of sulfuric and nitric acid are pumped through a nitration reactor (4) by means of a centrifugal pump (1) and reacted. The nitration reactor (4) is designed as a heat exchanger in which the reaction temperature is maintained between 120° F. (48.9° C.) and 150° C. (65.6° C.) by thermostatting (cf. the examples and patent claim 4). The reaction product obtained (comprising not only nitrobenzene but also an acid phase) is passed into a surge tank (11) operated under ambient pressure (cf. drain pipe 19). A first part of the liquid product mixture departing the surge tank (11) is recycled—without removing the acid phase—into the reaction via a first discharge line (16). The surge tank (11) therefore ensures, in conjunction with the drain pipe (19), that the centrifugal pump (1) is fed with the same mass flow of recycled product mixture even in the event of fluctuations in the production process (at least for a limited time) and that no inadmissibly high pressure can build up. A gas separation in the true sense of the word does not take place in this surge tank since, as a result of the low reaction temperature, it cannot be anticipated that any large proportions of a gas phase will form at all; lastly the boiling point of benzene at standard pressure, at 80° C., is far above the maximum temperature reported of 65.6° C. The arrangement depicted with a surge tank operated at ambient pressure is therefore due to the particular (circulation) mode.

A second part of the liquid product mixture departing the surge tank (11) is passed through a second discharge line (13) having a siphon equipped with a siphon breaker (15) and led via an overflow line (14) into a phase separation apparatus (not shown in FIG. 1) in which a phase separation into crude nitrobenzene and acid phase takes place. The siphon breaker (15) is apparently intended to prevent unintended complete emptying of the content of the surge tank (11) into the phase separation apparatus by reducing the suction effects.

In the adiabatic mode—which is currently more common and is also used in the present invention—cooling of the nitration reactor is omitted and therefore the exothermicity of the reaction, once unavoidable heat losses are disregarded, is reflected quantitatively in the temperature difference between the temperature on entry into the nitration reactor and the temperature of the completely converted product mixture (what is known as an adiabatic jump in temperature). In order that this temperature rise does not become excessive, adiabatically operated processes typically employ a very large sulfuric acid excess. A circulation regime as described in U.S. Pat. No. 3,092,671 B1 is not possible in such an adiabatic mode without relinquishing the economic advantages of this process at least to a certain extent, since here as a consequence of the adiabatic temperature jump the reaction product has a temperature which is much higher than the temperature of the mixed reactants before the start of the reaction. The comparatively high temperature of the reaction product is (after separation thereof into an acid phase and a nitrobenzene phase) needed for the flash evaporation of water contained in the acid phase. Recycling part of the reaction product prior to phase separation, as described in U.S. Pat. No. 3,092,671 B1, would necessitate cooling of the recycled fraction, which would impair the energy balance of the process and hence the economic viability thereof.

The reaction in adiabatic operating mode is generally conducted in such a way that the nitric acid and sulfuric acid are combined to give what is called the nitrating acid (also called mixed acid). Benzene is metered into this nitrating acid. This procedure is also preferably used in the process according to the invention. The reaction products are essentially water and nitrobenzene. In the nitration reaction, benzene, based on the molar amount of nitric acid, is used at least in a stoichiometric amount, but preferably in a 2% to 10% excess, so that the process product obtained in the nitration is essentially free from nitric acid. This process product is fed to a phase separation apparatus in which two liquid phases form, an organic phase and an aqueous phase. The organic phase is referred to as crude nitrobenzene and essentially consists of nitrobenzene, benzene and a certain amount of water and sulfuric acid dissolved in the nitrobenzene. The aqueous phase is referred to as waste acid and consists essentially of water, sulfuric acid and nitrobenzene dissolved in the sulfuric acid. In addition to these liquid constituents, the process product of the nitration also contains gaseous components, specifically firstly organic components such as evaporated benzene and low-boiling, non-aromatic secondary components (usually referred to as low boilers), and secondly inorganic components such as in particular nitrous gases ($NO_x$), formed as a result of side reactions of the nitric acid used. According to the prior art, these gaseous components separate from the two liquid phases in the phase separation apparatus and are discharged via a separate outlet as offgas stream. This offgas stream from the phase separation apparatus can be combined with the various offgas streams from other parts of the plant and worked up, where, as described in patent application EP 2 719 682 A1, benzene can be recovered and the nitrous gases can be converted to nitrous acid. In this way, the recovered benzene and the nitrous acid can be recycled and resupplied to the nitration.

The crude nitrobenzene formed in the reaction apparatuses and separated off from the acid phase in the phase separation apparatus is subjected to washing and a distillative workup according to the prior art. A characteristic feature of this workup is that unconverted excess benzene, after the wash, is separated off from nitrobenzene in a final distillation as "return benzene". This return benzene, which—in addition to the gas phase discharged in the phase separation apparatus—also contains a portion of the low-boiling, nonaromatic organic compounds (low boilers), is reused in the nitration reaction.

Patent application DE 10 2009 005324 A1 is concerned with problems which can accompany the high content of low boilers in the return benzene and describes, in this context, a process for preparing nitrobenzene by adiabatic nitration of benzene, in which the benzene/low boiler mixture obtained during the purification of the nitrobenzene is recycled to the nitration and the crude nitrobenzene is separated off from the sulfuric acid after the reaction under pressure.

The treatment of the offgas from the adiabatically performed nitration reaction with respect to nitrous gases is described in EP 0 976 718 A2. The offgas from the acid circuit and from the crude nitrobenzene is taken off, combined and sent via an $NO_x$ absorber in order to recover dilute nitric acid, which is returned into the reaction. The circulated sulfuric acid is concentrated in a flash evaporator and very substantially freed of organics. Traces of high-boiling organics such as nitrobenzene, dinitrobenzene and nitrophenols remain in the circulated acid and hence are also returned to the reaction.

Patent application WO 2014/016292 A1 describes how the nitrobenzene process may be better started up, by keeping the content of aliphatic organic compounds in the feed benzene during the startup time low (proportion by mass of less than 1.5%). This is achieved by adjusting the ratio of fresh benzene to return benzene during the startup time depending in particular on the purity of the return benzene, such that the stipulated maximum content of aliphatic organic compounds in the feed benzene is not exceeded. The proportion of return benzene during the startup time can also be zero; in this case only fresh benzene of sufficient purity is supplied to the nitration reactor during the startup time. Patent application WO 2014/016289 A1 describes how the continuous nitration of benzene to nitrobenzene in regular operation can be improved by limiting the content of aliphatic organic compounds in the feed benzene to a proportion by mass of less than 1.5%. In one embodiment, this is achieved by discharging low boilers with the gas phase of the phase separation apparatus. Both patent applications relate in particular to an improved product quality and optimized washing of the crude nitrobenzene; the influence of low boilers in the phase separation apparatus is not dealt with, however.

The phase separation apparatus (also called decanter) does not only have the important task of separating the process product of the nitration into an aqueous acidic phase and an organic phase containing crude nitrobenzene. In addition and as already mentioned, a gas phase containing benzene, low boilers and nitrous gases is also drawn off in the phase separation apparatus. A sufficiently high residence time therefore needs to be provided in the phase separation apparatus so that these physical processes (separation of the crude process product of the nitration into two liquid phases and a gas phase) can be performed without negatively impacting the production capacity of the plant. Due to the presence of the gas phase in the apparatus, the separation apparatus has to be designed much larger than would be the case for a pure liquid-liquid separation.

Operational practice has shown that problems can arise time and again in the phase separation of the crude process product of the nitration. These manifest, for example, in inadequate phase separation (e.g. entrainment of organics into the acid phase or formation of black deposits). These problems then arise to a greater degree when the crude process products of two or more, in particular independently controllable, nitration reactors operated in parallel, that is to say when conducting the reaction in two or more reaction lines (also referred to as reaction trains) operated in parallel, are passed into a common phase separation apparatus. This approach is not uncommon in practice. A multi-line reaction in conjunction with a single-line workup has often proven to be the best compromise between the requirements of minimizing investment costs on the one hand and maximizing flexibility in production on the other.

The efficiency of gas-liquid or liquid-liquid phase separation apparatuses can be increased according to the prior art by means of particular internals or a particular configuration of the entrance into the apparatus. This also applies to the phase separations in the nitrobenzene process (phase separation after the reaction and phase separations in the context of the washes). Internals such as plate internals, knitted meshes, lamellae and random packings may homogenize and stabilize the flow and enlarge the surface area, so that phenomena such as coalescence and the separation of droplets and bubbles proceed more quickly. Entry into the phase separation apparatus can be via baffles or deflecting plates which stabilize the flow or direct it towards the apparatus wall with the aim of increasing the residence time in the apparatus and hence of improving the separating efficiency. Established variants are described for example in *Gulf Equipment Guides*, Gas-Liquid and Liquid-Liquid Separators, chapter 3.5 (*Vessel Internals*) on pages 84 to 89, year 2009, by Maurice Stewart and Ken Arnold, and in *Fundamentals of Natural Gas Processing*, chapter 5, pages 105 to 117, year 2011, by Arthur J Kidnay, William R Parrish and Daniel G. McCartney. The variants described in the cited literature are explained in part using the example of gas-liquid phase separations, but are, as concerns the fundamental principles, also usable for liquid-liquid or triphasic gas-liquid-liquid separations. The disadvantage with the prior art processes is that deposits and fouling may occur as a result of the flow stabilization and the nature of the internals. For example, knitted meshes and lamellae become clogged over time and deposits form on the plates. The internals can be damaged by pressure shocks or excessively high flow velocities. Due to the corrosive media, the phase separation apparatuses are usually manufactured from enamel on the inside. The apparatuses can be damaged by the internals and maintenance or servicing of the apparatuses becomes more expensive.

There was therefore a need for further improvement in the preparation of nitrobenzene, in particular as concerns the efficiency of separation of the process product of the nitration into two liquid phases and a gaseous phase. It would be desirable in particular to configure as optimally as possible the discharge of the gaseous fraction and the separation of the two liquid phases from each other, both as concerns the quality of the separation and the process-engineering and apparatus configuration. This need is accommodated by the present invention both from a process engineering viewpoint and in terms of apparatus.

SUMMARY

It has surprisingly been found that problems observed time and time again in the liquid-liquid phase separation are associated with the simultaneously conducted discharge of the gas phase. Depending on the proportion of the gaseous phase, the presence thereof can lead to much greater velocities and turbulence in the liquid phases in the phase separation apparatus, which impedes the separation of the two liquid phases. In the event of fluctuating proportions or an increase in the gas phase, there may therefore be inadequate separation of the liquid phases, meaning that even greater proportions of organics may pass into the aqueous acidic phase. The following conclusions have been drawn: The presence of the gas phase in the separator generally leads to high velocities (and also to higher velocities of the liquid phases), since the gas phase moves at far greater velocities on account of the lower density compared to the liquid. Furthermore, the presence of the gas phase and the resulting triphasic gas-liquid-liquid separation also impairs the separating efficiency of the two liquid phases. Rising gas bubbles impede demixing of the liquid phases since mixing is constantly occurring again at the liquid-liquid phase boundary and the liquid phase with the higher density can be entrained together with the gas bubbles into the liquid phase with the lower density.

The present invention therefore firstly provides a process for the continuous preparation of nitrobenzene, in which
- a) a benzene-containing stream (a.1) is reacted under adiabatic conditions in a reactor with sulfuric acid (a.2) and nitric acid (a.3) using a, based on nitric acid (a.3), stoichiometric excess of benzene, to obtain a process product (a.4, henceforth also referred to as crude process product of the nitration) containing nitrobenzene, benzene and sulfuric acid;
- b) (i) the process product of the reaction of step a) containing nitrobenzene, benzene and sulfuric acid is first passed into a gas separator in which a gaseous phase (b.1) comprising benzene (which is used in excess and is partly evaporated) and gaseous secondary components is removed from this process product, leaving a liquid phase (b.2) comprising nitrobenzene (and also the unevaporated part of the unconverted (since it is used in excess) benzene) and sulfuric acid and depleted of gaseous constituents which is then
  (ii) passed into a phase separation apparatus and subjected there to a phase separation, wherein a liquid aqueous, sulfuric acid-comprising phase (b.3) and a liquid organic, nitrobenzene-comprising phase (b.4) are withdrawn from the phase separation apparatus;
- c) the liquid organic, nitrobenzene-comprising phase (b.4) from step b) is worked up to obtain nitrobenzene (c.1).

The present invention secondly provides a production plant for performing the process according to the invention for the continuous preparation of nitrobenzene, wherein the production plant comprises the following apparatuses:
- a) a reactor for the adiabatic reaction of a benzene-containing stream (a.1) with sulfuric acid (a.2) and nitric acid (a.3) using a, based on nitric acid (a.3), stoichiometric excess of benzene;
- b) (i) arranged downstream of the reactor of a), a gas separator for separating the process product from a) into a gaseous phase (b.1) comprising benzene and gaseous secondary components and a liquid phase (b.2) comprising nitrobenzene and sulfuric acid and depleted of gaseous constituents;
  (ii) arranged downstream of the gas separator of b)(i), a phase separation apparatus for separating the process product from b)(i) into a liquid aqueous, sulfuric acid-comprising phase (b.3) and a liquid organic, nitrobenzene-comprising phase (b.4);
- c) an apparatus for working up the liquid organic, nitrobenzene-comprising phase (b.4) from b)(ii) to give nitrobenzene (c.1), this apparatus in particular comprising the following devices:
  (i) devices for the single- or multi-stage washing of the liquid organic, nitrobenzene-comprising phase (b.4) and devices for removing unconverted benzene;
  (ii) devices for recycling the removed benzene from c)(i) into the reactor of a) as a constituent of the benzene-containing stream (a.1) used there;
- d) optionally, devices for concentrating the liquid aqueous, sulfuric acid-comprising phase (b.3) from b)(ii) by evaporation of water and devices for recycling the liquid aqueous phase (d.1) thus obtained comprising a higher concentration of sulfuric acid compared to phase (b.3) into the reactor of a) as constituent of the sulfuric acid (a.2) used there.

In the terminology of the present invention, the term "gaseous secondary components" encompasses at least the low boilers already mentioned hereinabove, low boilers being understood as being all nonaromatic, organic secondary components of the process product of the nitration (=step a)) which have boiling points at standard pressure (1013 mbar) lying below that of nitrobenzene. Typical low boilers are n-heptane, dimethylcyclopentane, 3-ethylpentane, cyclohexane, the isomeric dimethylpentanes, n-hexane, cyclopentane, n-pentane, trimethylcyclopentane, methylcyclohexane, ethylcyclopentane and octane. In addition, inorganic secondary components may also be present, in particular such as the nitrous gases already mentioned.

In the process according to the invention, the liquid phase (b.2) comprising nitrobenzene and sulfuric acid and depleted of gaseous constituents obtained in step b)(i) is sent to the phase separation of step b)(ii), specifically without recycling part of this liquid phase (b.2) into the reaction of step a). A reaction loop, as described in the prior art for isothermal processes, is not subject matter of the process according to the invention. The same applies, of course, for the production plant according to the invention; this does not have devices for recycling the liquid phase (b.2) comprising nitrobenzene and sulfuric acid and depleted of gaseous constituents obtained in the gas separator [b)(i)] into the reactor [a)].

DETAILED DESCRIPTION

Figure 1:
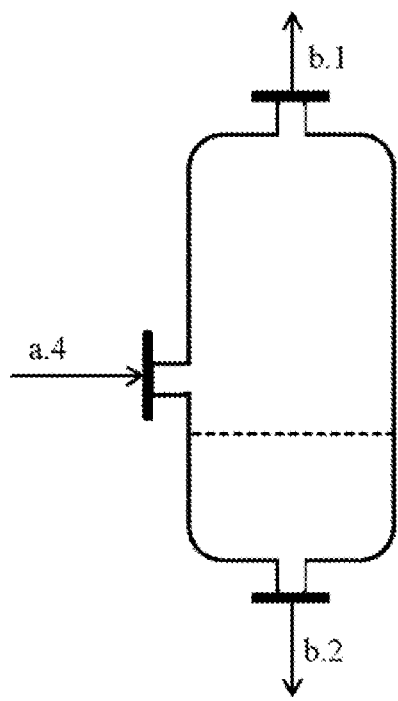
FIG. 1 shows a vertically arranged gas separator in which the process product (a.4) is fed at the side, the gas phase (b.1) is discharged at the top and the liquid phase (b.2) is discharged at the bottom.

There follows firstly a brief summary of various possible embodiments.

In a first embodiment of the process according to the invention, which can be combined with all other embodiments, in a step d) the liquid aqueous, sulfuric acid-comprising phase (b.3) obtained in step b)(ii) is concentrated by evaporation of water to give a liquid aqueous phase (d.1) comprising a higher concentration of sulfuric acid compared to phase (b.3), this phase (d.1) being recycled into step a) and used as constituent of the sulfuric acid (a.2) used there.

In a second embodiment of the process according to the invention, which can be combined with all other embodiments, the workup of the liquid organic, nitrobenzene-comprising phase (b.4) in step c) comprises the steps:
  (i) washing (in one or multiple stages) the liquid organic, nitrobenzene-comprising phase (b.4) and removing unconverted benzene (c.2),
  (ii) using removed benzene (c.2) as a constituent of the benzene used in step a).

In a third embodiment of the process according to the invention, which can be combined with all other embodiments, the stoichiometric excess of benzene based on nitric acid in step a) is set to a value in the range from 2.0% to 40% of theory, preferably 3.0% to 30%, particularly preferably 4.0% to 25%, of theory.

In a fourth embodiment of the process according to the invention, which can be combined with all other embodiments, the temperature in the reactor of step a) is maintained in the range from 98° C. to 140° C.

In a fifth embodiment of the process according to the invention, which can be combined with all other embodiments, step a) is performed in a plurality of, preferably in 2 to 5, particularly preferably in 2 to 3, reactors operated in parallel, wherein
  (α) the process products (a.4) containing nitrobenzene, benzene and sulfuric acid that are obtained in each of these reactors are combined prior to performing step b)(i);
  or
  (β) the process products (a.4) containing nitrobenzene, benzene and sulfuric acid that are obtained in each of these reactors are each passed in step b)(i) into a dedicated gas separator and the liquid phases (b.2) obtained there comprising nitrobenzene and sulfuric acid and depleted of gaseous constituents are combined (β)(1) in the phase separation apparatus of step b)(ii) or (β)(2) prior to performing step b)(ii);
  or
  (γ) the process products (a.4) containing nitrobenzene, benzene and sulfuric acid that are obtained in each of these reactors are passed in step b)(i) into a common gas separator without prior combining.

In a sixth embodiment of the process according to the invention, which can be combined with all other embodiments, the gas separator used is a gravitational separator or a centrifugal separator.

In a seventh embodiment of the process according to the invention, which is a particular configuration of the sixth embodiment, the gas separator used is a gravitational separator.

In an eighth embodiment of the process according to the invention, which is a particular configuration of the seventh embodiment, the gravitational separator used is a horizontally or vertically arranged gravitational separator to which the process product (a.4) containing nitrobenzene, benzene and sulfuric acid
  is fed from the side or from the bottom, wherein the gaseous phase (b.1) comprising benzene and gaseous secondary components is withdrawn from the gravitational separator as a top stream and the liquid phase (b.2) comprising nitrobenzene and sulfuric acid and depleted of gaseous constituents is withdrawn from the gravitational separator as a bottom stream at the bottom or from the side, or
  is fed from the top, wherein the gaseous phase (b.1) comprising benzene and gaseous secondary components is withdrawn from the gravitational separator from the side and the liquid phase (b.2) comprising nitrobenzene and sulfuric acid and depleted of gaseous constituents is withdrawn from the gravitational separator at the bottom.

In a ninth embodiment of the process according to the invention, which is a particular configuration of the sixth embodiment, the gas separator used is a centrifugal separator.

In a tenth embodiment of the process according to the invention, which is a particular configuration of the ninth embodiment, the centrifugal separator used is a vertically arranged, cylindrical, conical or cylindrical-conical cyclone through which the process product (a.4) containing nitrobenzene, benzene and sulfuric acid is guided with the generation of swirl, wherein the gaseous phase (b.1) comprising benzene and gaseous secondary components is discharged towards the top and the liquid phase (b.2) comprising nitrobenzene and sulfuric acid and depleted of gaseous constituents is discharged towards the bottom.

In an eleventh embodiment of the process according to the invention, which can be combined with all other embodiments, the reactor used in step a) is a tubular reactor, which is preferably arranged vertically and has two or more (preferably 2 to 15, particularly preferably 4 to 12, excluding the mixing device used for the initial mixing of benzene with nitric and sulfuric acid) dispersing elements, a flow through the tubular reactor particularly preferably being effected from bottom to top (i.e. the starting materials benzene-containing stream (a.1), sulfuric acid (a.2) and nitric acid (a.3) are fed to the vertically arranged tubular reactor at the bottom and the process product (a.4) containing nitrobenzene, benzene and sulfuric acid is withdrawn from the tubular reactor at the top). If the process includes the use of a plurality of reactors, as in the fifth embodiment, this preferably applies to all reactors.

In a first embodiment of the production plant according to the invention, this has the following:
a) a plurality of, preferably two to five, particularly preferably two to three, (in particular independently controllable) reactors operated in parallel for the adiabatic reaction of a benzene-containing stream (a.1) with sulfuric acid (a.2) and nitric acid (a.3) using a, based on nitric acid (a.3), stoichiometric excess of benzene and in a variant (α),
b) (i-0) arranged downstream of the reactors of a), devices for combining the process products containing nitrobenzene, benzene and sulfuric acid that are obtained in these reactors to form a mixed stream and for introducing the mixed stream into
   (i) a gas separator, arranged downstream of the devices for combining and introducing of b)(i-0), for separating the mixed stream from b)(i-0) into a gaseous phase (b.1) comprising benzene and gaseous secondary components and a liquid phase (b.2) comprising nitrobenzene and sulfuric acid and depleted of gaseous constituents, and
   (ii) a phase separation apparatus, arranged downstream of the gas separator of b)(i), for separating the liquid phase (b.2) comprising nitrobenzene and sulfuric acid and depleted of gaseous constituents into a liquid aqueous, sulfuric acid-comprising phase (b.3) and a liquid organic, nitrobenzene-comprising phase (b.4);
or, in a variant (β),
b) (i) arranged downstream of the reactors of a), a plurality of gas separators operated in parallel for separating the process product of each reactor of a) into a gaseous phase (b.1) comprising benzene and gaseous secondary components and a liquid phase (b.2) comprising nitrobenzene and sulfuric acid and depleted of gaseous constituents, and
   (ii) a phase separation apparatus, arranged downstream of the gas separators of b)(i), for separating the liquid process product from b)(i) into a liquid aqueous, sulfuric acid-comprising phase (b.3) and a liquid organic, nitrobenzene-comprising phase (b.4),
   wherein optionally devices for combining the liquid phases (b.2) comprising nitrobenzene and sulfuric acid and depleted of gaseous constituents that are obtained in the gas separators are arranged between the plurality of gas separators operated in parallel of b)(i) and the phase separation apparatus of b)(ii);
or, in a variant (γ),
b) (i) arranged downstream of the reactors of a), a gas separator (common to all reactors) for separating the process products of the reactors of a) into a gaseous phase (b.1) comprising benzene and gaseous secondary components and a liquid phase (b.2) comprising nitrobenzene and sulfuric acid and depleted of gaseous constituents, and
   (ii) a phase separation apparatus, arranged downstream of the gas separator of b)(i), for separating the liquid phase (b.2) from b)(i) comprising nitrobenzene and sulfuric acid and depleted of gaseous constituents into a liquid aqueous, sulfuric acid-comprising phase (b.3) and a liquid organic, nitrobenzene-comprising phase (b.4).

In a second embodiment of the production plant according to the invention, which can be combined with all other embodiments, the reactor of a) is a tubular reactor, which is preferably arranged vertically and has two or more (preferably 2 to 15, particularly preferably 4 to 12, excluding the mixing device used for the initial mixing of benzene with nitric and sulfuric acid) dispersing elements, a flow through the tubular reactor particularly preferably being effected from bottom to top (i.e. the starting materials benzene-containing stream (a.1), sulfuric acid (a.2) and nitric acid (a.3) are fed to the vertically arranged tubular reactor at the bottom and the process product (a.4) containing nitrobenzene, benzene and sulfuric acid is withdrawn from the tubular reactor at the top). If the production plant includes a plurality of reactors, as in the first embodiment, this preferably applies to all reactors.

The embodiments briefly outlined above and further possible configurations of the invention are elucidated in detail hereinafter. The abovementioned embodiments and further possible configurations may be combined with one another as desired, unless the opposite is apparent from the context.

Step a) of the process according to the invention, the nitration of the benzene-containing stream (a.1) in a reactor with sulfuric acid (a.2) and nitric acid (a.3) using a, based on nitric acid (a.3), stoichiometric excess of benzene, can in principle be conducted by any adiabatically operated nitration process known from the prior art.

It is preferable to first meter the nitric acid (a.3) and then the benzene-containing stream (a.1) into the sulfuric acid (a.2). The premixing of nitric acid (a.3) and sulfuric acid (a.2) produces the so-called mixed acid into which in this embodiment the benzene-containing stream (a.1) is then metered in. In this case, the mixed acid used contains, based on the total mass of the mixed acid, preferably at least 2.0% by mass of nitric acid and at least 66.0% by mass of sulfuric acid, particularly preferably 2.0% by mass to 4.0% by mass of nitric acid and 66.0% by mass to 75.0% by mass of sulfuric acid.

The stoichiometric excess of benzene based on nitric acid (a.3) is preferably set to a value in the range from 2.0% to 40%, particularly preferably in the range from 3.0% to 30%, very particularly preferably in the range from 4.0% to 25%, of theory. Theoretically, 1 mol of $HNO_3$ reacts with 1 mol of benzene. A benzene excess of x % in relation to $HNO_3$ therefore corresponds to a molar ratio n(benzene)/n($HNO_3$) (n=molar amount) of $$\frac{1 + \frac{x}{100}}{1},$$

i.e. for example $$\frac{1 + \frac{2}{100}}{1} = 1.02$$

with a 2% benzene excess or for example $$\frac{1 + \frac{40}{100}}{1} = 1.40$$

with a 40% benzene excess.

It is preferable to recover excess benzene and use it in part or in full as a constituent of the benzene-containing stream (a.1). The excess benzene (c.2) is recovered in this case before or after, especially after, a single- or multi-stage washing of the crude nitrobenzene; for further details reference can be made to the discussion of step c) hereinbelow. The benzene-containing stream (a.1) is therefore preferably a mixture of benzene freshly fed to the reaction (referred to as fresh benzene) and recycled benzene (referred to as return benzene). In any case, the reaction conditions are in particular selected so that the proportion by mass of benzene in the benzene-containing stream (a.1), based on the total mass of the benzene-containing stream (a.1), is at least 90.0%, preferably at least 95.0%, particularly preferably at least 98.5%.

According to the invention, step a) is conducted under adiabatic conditions. In the case of adiabatic reaction regime, the reactor used in step a) is neither heated nor cooled; the reaction temperature results from the temperature of the reactants used and the mixing ratio between them. The reactor is preferably well insulated in order to reduce heat losses to a minimum. If the nitration is conducted adiabatically, the reaction temperature of the mixture reacting in the reactor thus increases from the "starting temperature" immediately after the first mixing of the reactants up to the "end temperature" after maximum conversion and is preferably maintained constantly at values in the range from 98° C. to 140° C. The starting temperature results from the temperatures of the feedstocks benzene, sulfuric acid and nitric acid, from the concentrations of the acids used, from the quantitative ratio between them and from the volumetric ratio of organic phase (benzene) to aqueous phase (sulfuric and nitric acid), what is known as the phase ratio. The phase ratio is also decisive for the end temperature: The smaller the phase ratio (thus the more sulfuric acid present), the lower the end temperature. In the case of the preferred use of a tubular reactor (see hereafter), the temperature rises as a result of increasing conversion along the longitudinal axis of the reactor. At the entry into the reactor the temperature is in the lower region of the mentioned temperature range of 98° C. to 140° C., at the exit from the reactor the temperature is in the upper region of the mentioned temperature range.

Preferably, step a) is executed in a process regime as described in DE 10 2008 048 713 A1, especially paragraph [0024].

Suitable reactors for step a) are in principle any reactors known in the prior art for adiabatic nitrations, such as stirred tanks (especially stirred tank cascades) and tubular reactors. Tubular reactors are preferred. Particular preference is given here to a tubular reactor in which two or more dispersing elements are distributed over the length of the tubular reactor, these ensuring intense mixing of benzene, nitric acid and sulfuric acid. Particular preference is given to using a vertically arranged tubular reactor in which two or more (preferably 2 to 15, particularly preferably 4 to 12, excluding the mixing device used for the initial mixing of benzene with nitric and sulfuric acid) dispersing elements are distributed over the length of the tubular reactor. The flow through such a tubular reactor is very particularly preferably from bottom to top. Such a reactor, and the form of usable dispersing elements, are described for example in EP 1 291 078 A2 (see there FIG. 1).

In step b) of the process according to the invention, the process product (a.4) containing nitrobenzene, benzene and sulfuric acid (and also secondary components which may be present in the gas phase or in dissolved form) from step a) is first (i) depleted of gaseous constituents and then subjected to (ii) a phase separation in a phase separation apparatus.

Step b)(i), the gas-liquid phase separation, is effected here in a gas separator. Gas separators which can be used are in principle all separators known to those skilled in the art which enable a gas-liquid separation. Possible apparatuses for the separation of gaseous and liquid streams are general knowledge for those skilled in the art. Details concerning the various processes and equipment for separating gaseous and liquid streams can be found in the specialist literature, such as for example in *Oilfield Processing, Crude Oil*, Vol. 2, chapter 6, pages 79 to 112, year 1995, by Manning, Francis S. and Thompson, Richard E. or in *Gulf Equipment Guides, Gas-Liquid and Liquid-Liquid Separators*, chapters 3.3 to 3.5 on pages 72 to 103, year 2009, by Maurice Stewart and Ken Arnold. The variants described in the cited literature are explained in part using the example of triphasic gas-liquid-liquid separations, but are also usable for gas-liquid phase separations as concerns the fundamental principles. The separation of the steps (i) removal of (at least the majority of) the gas phase from the two liquid phases and (ii) separation of the two liquid phases from each other is essential to the invention. Therefore, according to the invention these steps are performed in two apparatuses, the gas separator and the phase separation apparatus. However, in terms of the apparatus configuration, the gas separator and the phase separation apparatus may by all means share common features.

Preference is given to using gravitational separators or centrifugal separators as gas separator.

In one embodiment of the invention, the gas separator is a horizontally or vertically arranged gravitational separator to which the process product (a.4) of the conversion of step a) containing nitrobenzene, benzene and sulfuric acid

- is fed from the side or from the bottom, wherein the gaseous phase (b.1) comprising benzene and gaseous secondary components is withdrawn from the gravitational separator as a top stream and the liquid phase (b.2) comprising nitrobenzene and sulfuric acid and depleted of gaseous constituents is withdrawn from the gravitational separator as a bottom stream at the bottom or from the side, or
- is fed from the top, wherein the gaseous phase (b.1) comprising benzene and gaseous secondary components is withdrawn from the gravitational separator from the side and the liquid phase (b.2) comprising nitrobenzene and sulfuric acid and depleted of gaseous constituents is withdrawn from the gravitational separator at the bottom.

Figure 2:
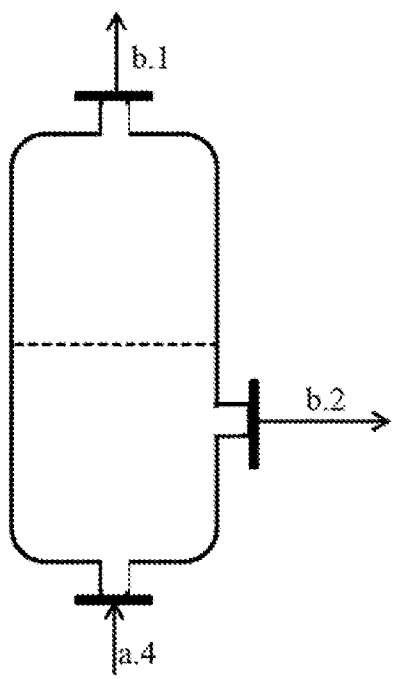
FIG. 2 shows a vertically arranged gas separator in which the process product (a.4) is fed at the bottom, the gas phase (b.1) is discharged at the top and the liquid phase (b.2) is discharged from the side.
Figure 3:
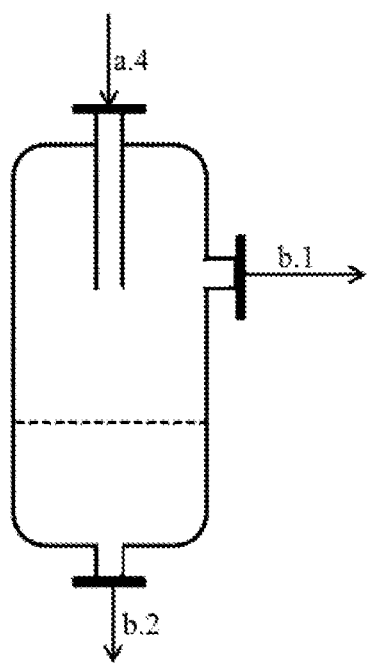
FIG. 3 shows a vertically arranged gas separator in which the process product (a.4) is fed at the top, the gas phase (b.1) is discharged from the side and the liquid phase (b.2) is discharged at the bottom.

The expression "horizontally or vertically arranged" relates to the longitudinal axis of the essentially cylindrical apparatus. FIG. 1 to FIG. 3 show vertically arranged gravitational separators which can be used in step b)(i):

In the gas separator according to FIG. 1, the process product (a.4) is fed from the side, the gas phase (b.1) is discharged at the top and the liquid phase (b.2) is discharged at the bottom.

In the gas separator according to FIG. 2, the process product (a.4) is fed at the bottom, the gas phase (b.1) is discharged at the top and the liquid phase (b.2) is discharged from the side.

In the gas separator according to FIG. 3, the process product (a.4) is fed at the top, the gas phase (b.1) is discharged from the side and the liquid phase (b.2) is discharged at the bottom.

Preference is given to a configuration according to FIG. 1.

However, it is also possible to use a centrifugal separator. Preference is given here to a vertically arranged, cylindrical, conical or cylindrical-conical cyclone through which the process product (a.4) containing nitrobenzene, benzene and sulfuric acid is guided with the generation of swirl, wherein the gaseous phase 5 (b.1) comprising benzene and gaseous secondary components is discharged towards the top and the liquid phase (b.2) comprising nitrobenzene and sulfuric acid and depleted of gaseous constituents is discharged towards the bottom. The term "arranged vertically" again relates to the longitudinal axis of the apparatus. The swirl can be generated either through a tangentially arranged entry connection or a deflecting plate (see FIG. 3.20 in Gulf Equipment Guides: Gas-liquid and liquid-liquid Separators, Stewart & Arnold, 2009, Gulf Professional Publishing).

The liquid-liquid phase separation in step b)(ii) is effected by methods known per se from the prior art in a phase separation apparatus known to those skilled in the art. The aqueous phase (b.3) essentially contains (as a result of the formation of water of reaction and due to the introduction of water into the reaction from the nitric acid used) dilute sulfuric acid alongside inorganic impurities, the organic phase (b.3) essentially contains nitrobenzene alongside excess benzene and organic impurities. The phase separation apparatus is preferably provided with a gas outlet via which any remaining proportions of gaseous constituents can be discharged. The gas outlet of the gas separator of step b)(i) and the gas outlet of the phase separation apparatus of step b)(ii) preferably open out into a common offgas workup apparatus. The gas separator is preferably not temperature-controlled, as a result of which the temperatures in the gas separator result from the temperature of the inflowing reaction mixture (see step a)). The gas separator is preferably operated at slightly elevated pressure with respect to ambient pressure ("positive pressure"), the pressure in the gas space of the gas separator being 50 mbar to 100 mbar, for example 80 mbar, above ambient pressure. The phase separation apparatus of step b)(ii) is also preferably not temperature-controlled and is preferably operated at slight positive pressure, the same values in particular being observed as in the gas separator (i.e. 50 mbar to 100 mbar, for example 80 mbar, above ambient pressure, measured in the gas space).

Irrespective of the precise mode and the precise configuration of the reactor in step a) and of the gas separation and phase separation in step b), it is preferable to concentrate the liquid aqueous, sulfuric acid-comprising phase (b.3) obtained in step b) by evaporation of water to give a liquid aqueous phase (d.1) comprising a higher concentration of sulfuric acid compared to phase (b.3), to recycle it into step a) and to use it in part or in full as constituent of the sulfuric acid (a.2) used there. In this case, the sulfuric acid (a.2) used in step a) therefore contains recycled sulfuric acid (d.1) and in certain embodiments can even consist thereof. This preferred process regime is referred to in the terminology of the present invention as step d) and is explained in yet more detail below.

In step c) of the process according to the invention, the liquid phase (b.4) obtained in step b)(ii) (the crude nitrobenzene) is worked up to obtain nitrobenzene (c.1). This workup can in principle be accomplished as known in the prior art. A preferred procedure is outlined below:

First, the organic phase (b.4) is washed in one or more stages (step c)(i)). In a first substep of this wash, the organic phase (b.4), which typically still contains traces of acid, is washed in one or more stages with an aqueous washing liquid and then separated from the acidic aqueous phase obtained by phase separation, in the case of two or more washing stages after each individual washing stage. In this operation, the acid residues contained in the crude nitrobenzene (b.4) are washed out; this process step is therefore also referred to as acidic wash. This step is sufficiently well known from the prior art and is therefore outlined only briefly here. Preferably, for performance of this acidic wash, aqueous streams obtained in operation are recycled.

The organic phase thus obtained is then, in a second substep in an alkaline wash, washed in one or more stages with an aqueous solution of a base, preferably selected from sodium hydroxide, sodium carbonate or sodium hydrogencarbonate, and then separated from the alkaline wash water by phase separation, in the case of two or more washing stages after each individual washing stage. Particular preference is given to using sodium hydroxide solution as aqueous base solution. This step is sufficiently well known from the prior art and is therefore outlined only briefly here. The pH of the sodium hydroxide solution used and its mass ratio to the organic phase are adjusted such that acidic impurities (for example nitrophenols formed as by-products and acid residues incompletely removed in the first substep) are neutralized in the alkaline wash. The subsequent workup of the alkaline wastewater can be effected by the methods of the prior art, for example according to the teaching of EP 1 593 654 A1 and EP 1 132 347 A2.

The organic phase thus obtained is lastly, in a third substep in a neutral wash, washed in one or more stages with water and then separated from the aqueous phase by phase separation, in the case of two or more washing stages after each individual washing stage. This can in principle be accomplished by any methods that are customary in the prior art. The washing water used here is preferably demineralized water, more preferably a mixture of demineralized water and steam condensate (i.e. a condensate of steam which has been obtained by heat exchange of water with any exothermic process steps), and most preferably steam condensate. Preference is given to a procedure in which an electrophoresis is used in the last neutral stage of the neutral wash (see WO 2012/013678 A2).

The nitrobenzene washed in this way is lastly freed of dissolved water, unconverted benzene and any organic impurities by further workup (step c)(ii)). This workup is preferably effected by distillation, wherein the vapors of water and benzene and any organic impurities are driven off overhead. The vapors are cooled and run into a separating vessel. Water separates out in the lower phase and is removed. In the upper phase are benzene and low boilers, which are fed back to the reaction as return benzene. If necessary, a portion of this upper phase can be discharged (that is to say, not recycled) in order to avoid excessive accumulation of low boilers. It is also possible to separate low boilers off from this upper phase and to feed a return benzene depleted of low boilers to the reaction. The distillation apparatus used is preferably a rectification column. The bottom product from the distillation, optionally after a further distillation in which nitrobenzene is obtained as distillate (i.e. as topstream or sidestream product), is sent to further applications (such as in particular hydrogenation to aniline) as (pure) nitrobenzene (c.1).

Alternatively to the procedure presented here, it is also conceivable to remove excess benzene prior to the wash.

As already mentioned, it is preferable in a step d) to concentrate the liquid aqueous, sulfuric acid-comprising phase (b.3) obtained in step b)(ii) by evaporation of water to give a liquid aqueous phase (d.1) comprising a higher concentration of sulfuric acid compared to phase (b.3), to recycle it in part or in full into step a) and to use it as constituent of the sulfuric acid (a.2) used there. This concentration of the aqueous phase (b.3) can in principle be effected as known from the prior art. Preference is given to an embodiment in which the sulfuric acid in the aqueous phase (b.3) is concentrated in a flash evaporator by evaporating water into a region of reduced pressure. In the adiabatic mode provided according to the invention it is possible, given correct choice of the reaction conditions, to achieve such significant heating in step a) of the sulfuric acid-containing aqueous phase (b.3) with the heat of reaction of the exothermic reaction that, in the flash evaporator, the concentration and temperature of the sulfuric acid-containing aqueous phase that it had prior to the reaction with benzene and nitric acid on entry into the reactor space can simultaneously be established again, that is to say (d.1) corresponds to (a.2) in terms of temperature and concentration. This is described in EP 2 354 117 A1, especially paragraph [0045].

It is possible to perform the nitration in step a) in a plurality of (in particular independently controllable) reactors operated in parallel (that is to say in a plurality of so-called reaction lines or reaction trains). In this case, (α) the process products (a.4) containing nitrobenzene, benzene and sulfuric acid that are obtained in each of these reactors can be combined prior to performing step b)(i);

or (β) the process products (a.4) containing nitrobenzene, benzene and sulfuric acid that are obtained in each of these reactors can each be passed in step b)(i) into a dedicated gas separator and the liquid phases (b.2) obtained there comprising nitrobenzene and sulfuric acid and depleted of gaseous constituents can be combined either (β)(1) in the phase separation apparatus of step b)(ii)

or (β)(2) prior to performing step b)(ii);

or (γ) the process products (a.4) containing nitrobenzene, benzene and sulfuric acid that are obtained in each of these reactors are passed in step b)(i) into a common gas separator without prior combining.

Preferably in this embodiment, two to five reactors, particularly preferably two to three reactors, are operated in parallel.

Preference is given to the variants (α), (β)(2) and (γ). The homogenization of the nitrated reaction solutions from the individual reaction lines which is effected in these variants prior to the liquid-liquid phase separation in step b)(ii) leads to a reduction or avoidance of turbulence on entry into the phase separation apparatus of step b)(ii). Undesired flows in the phase separation apparatus, such as crossflows and backflows and also swirl formation, which form due to different proportions of the three phases (aqueous, organic, gas) in the incoming reaction solutions, can be reduced or eliminated. Particular preference is given to the variants (α), (β)(2) since in these advantages in these variants can also be achieved in the gas separator of (b)(i). Combining of the nitrated reaction solutions from the individual reaction lines prior to step b)(i) is the simplest in terms of apparatus, and therefore very particular preference is given to the variant (α).

In the variants (α), (β)(2) and (γ), the phase separation apparatus of step b)(ii) is fed with a mixed stream, originating from all parallel-operated reactors, of the liquid phase (b.2) comprising nitrobenzene and sulfuric acid and depleted of gaseous constituents. This mixed stream can be fed to the phase separation apparatus via a (single) inlet connection. However, it is also possible to divide this mixed stream (b.2) back into a plurality of (preferably 2 to 5, particularly preferably 2 to 3) substreams and to feed these substreams to the phase separation apparatus at spatially different locations via a number of inlet connections corresponding to the number of substreams. Once the aforementioned homogenization of the nitrated reaction solutions from the individual parallel-operated reactors has been performed, only a single, uniform process product remains having a given temperature and chemical composition (the mixed stream). By again dividing this uniform process product into substreams, the temperature and composition of the individual substreams are not altered further with respect to the single uniform process product, meaning that this procedure does not detract from the abovementioned advantages of the homogenization. Therefore, with this procedure, too, the substreams fed to the phase separation apparatus are in homogenized form with respect to their velocities, temperatures and chemical compositions at the entrances to the phase separation apparatus. The procedure using two or more inlet connections into the phase separation apparatus has the advantage that the velocities at the individual inlet connections (for an identical diameter) and also in general the inlet and mixing processes are markedly reduced, and the phase separation can begin more rapidly.

As already mentioned, the present invention secondly provides a production plant for performing the process according to the invention for the continuous preparation of nitrobenzene. Preferred embodiments and configurations of the process according to the invention apply likewise correspondingly to the production plant according to the invention. For example, the production plant according to the invention preferably comprises a tubular reactor as reactor.

Figure 4:
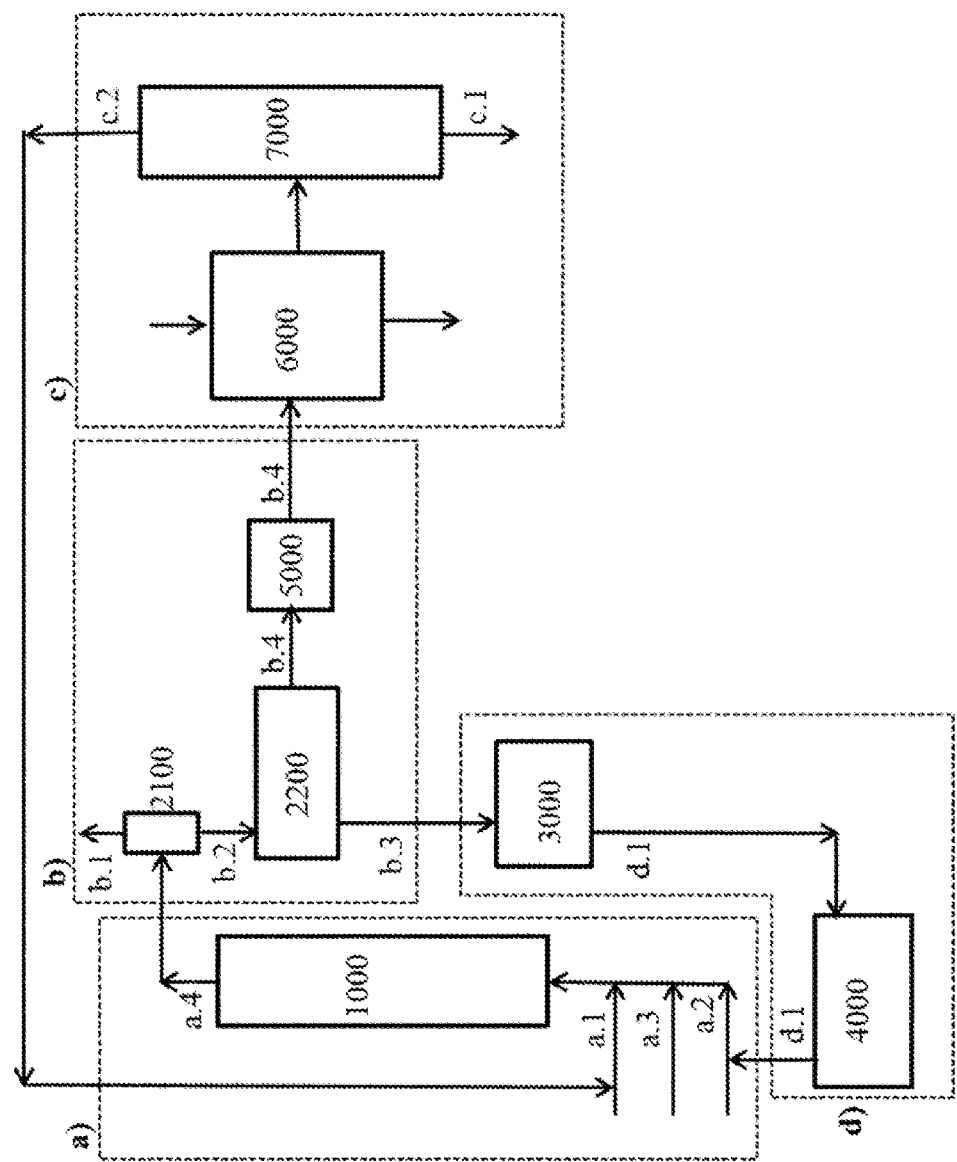
FIG. 4 shows a possible configuration of a production plant according to the invention.

The appended drawing FIG. 4 shows a possible configuration of the production plant according to the invention. The following references apply in the drawing:

1000: Reactor
2100: Gas separator
2200: Phase separation apparatus
3000: Device for sulfuric acid concentration (evaporator)
4000: Sulfuric acid tank
5000: Crude nitrobenzene tank
6000: Devices for single- or multi-stage washing of the crude nitrobenzene
7000: Device for removing unconverted benzene (in particular rectification column)

In a particular embodiment, the production plant according to the invention comprises a plurality of (in particular independently controllable) reactors operated in parallel (that is to say a plurality of so-called reaction lines or reaction trains). In this case, there are a number of possibilities for further configuring the production plant:

(α) The production plant can have a device, arranged downstream of the reactors operated in parallel, for combining the process products containing nitrobenzene, benzene and sulfuric acid obtained in the reactors. Such a device is for example a vessel which is connected via lines to the exit openings for the crude process products of the nitration from the reactors. The crude process products of the nitration are combined in this vessel and then the combined crude process product of the nitration is passed into a gas separator (common to all reactors operated in parallel). Instead of a vessel, the individual lines from the exit openings for the crude process products of the nitration from the reactors can also be led simply via connecting pieces (in the simplest case of two reactors a T connector) into a common pipe which opens into the gas separator.

From the gas separator onwards, the production plant in this embodiment is thus constructed as in the case of use of a single reactor (possibly aside from larger designs of the apparatuses since a plurality of parallel-operated reactors are typically used when particularly large amounts of nitrobenzene are intended to be prepared).

(β) However, it is also possible to connect a plurality of parallel-operated gas separators downstream of the plurality of parallel-operated reactors, the liquid exits of these gas separators opening into a single phase separation apparatus (common to all parallel-operated gas separators) of b)(ii). This can be realized (1) such that a line leads from the liquid exit of each gas separator into the phase separation apparatus, so that the individual liquid phases (b.2) comprising nitrobenzene and sulfuric acid and depleted of gaseous constituents are first combined in the phase separation apparatus. However, it is preferable (2) to already combine these liquid phases prior to entry into the phase separation apparatus. This is accomplished via a corresponding combining device, which can be designed exactly as described above for the configuration with a single gas separator.

(γ) The process products (a.4) containing nitrobenzene, benzene and sulfuric acid that are obtained in each of the reactors can also be passed into a common gas separator without prior combining.

Preference is given to the variants (α), (β)(2) and (γ), and particular preference is given to the variants (α) and (β)(2).

In the embodiment with a plurality of reaction lines, the production plant according to the invention therefore preferably comprises a) a plurality of (in particular independently controllable) reactors operated in parallel for the adiabatic reaction of a benzene-containing stream (a.1) with sulfuric acid (a.2) and nitric acid (a.3) using a, based on nitric acid (a.3), stoichiometric excess of benzene and in a variant (α), b) (i-0) arranged downstream of the reactors of a), devices for combining the process products containing nitrobenzene, benzene and sulfuric acid that are obtained in these reactors to form a mixed stream and for introducing the mixed stream into (i) a gas separator, arranged downstream of the devices for combining and introducing of b)(i-0), for separating the mixed stream from b)(i-0) into a gaseous phase (b.1) comprising benzene and gaseous secondary components and a liquid phase (b.2) comprising nitrobenzene and sulfuric acid and depleted of gaseous constituents, and (ii) a phase separation apparatus, arranged downstream of the gas separator of b)(i), for separating the liquid phase (b.2) comprising nitrobenzene and sulfuric acid and depleted of gaseous constituents into a liquid aqueous, sulfuric acid-comprising phase (b.3) and a liquid organic, nitrobenzene-comprising phase (b.4);

or, in a variant (β), b) (i) arranged downstream of the reactors of a), a plurality of gas separators operated in parallel for separating the process product of each reactor of a) into a gaseous phase (b.1) comprising benzene and gaseous secondary components and a liquid phase (b.2) comprising nitrobenzene and sulfuric acid and depleted of gaseous constituents, and (ii) a phase separation apparatus, arranged downstream of the gas separators of b)(i), for separating the liquid process product from b)(i) into a liquid aqueous, sulfuric acid-comprising phase (b.3) and a liquid organic, nitrobenzene-comprising phase (b.4), wherein optionally (and preferably) devices for combining the liquid phases (b.2) comprising nitrobenzene and sulfuric acid and depleted of gaseous constituents that are obtained in the gas separators are arranged between the plurality of gas separators operated in parallel of b) (i) and the phase separation apparatus of b) (ii);

or, in a variant (γ), b) (i) arranged downstream of the reactors of a), a gas separator (common to all reactors) for separating the process products of the reactors of a) into a gaseous phase (b.1) comprising benzene and gaseous secondary components and a liquid phase (b.2) comprising nitrobenzene and sulfuric acid and depleted of gaseous constituents, and (ii) a phase separation apparatus, arranged downstream of the gas separator of b)(i), for separating the liquid phase (b.2) from b)(i) comprising nitrobenzene and sulfuric acid and depleted of gaseous constituents into a liquid aqueous, sulfuric acid-comprising phase (b.3) and a liquid organic, nitrobenzene-comprising phase (b.4).

In all configurations of this embodiment, the production plant preferably comprises two to five reactors operated in parallel, particularly preferably two to three reactors operated in parallel. In the variant (β), the number of gas separators operated in parallel corresponds to the number of reactors operated in parallel.

Figure 5:
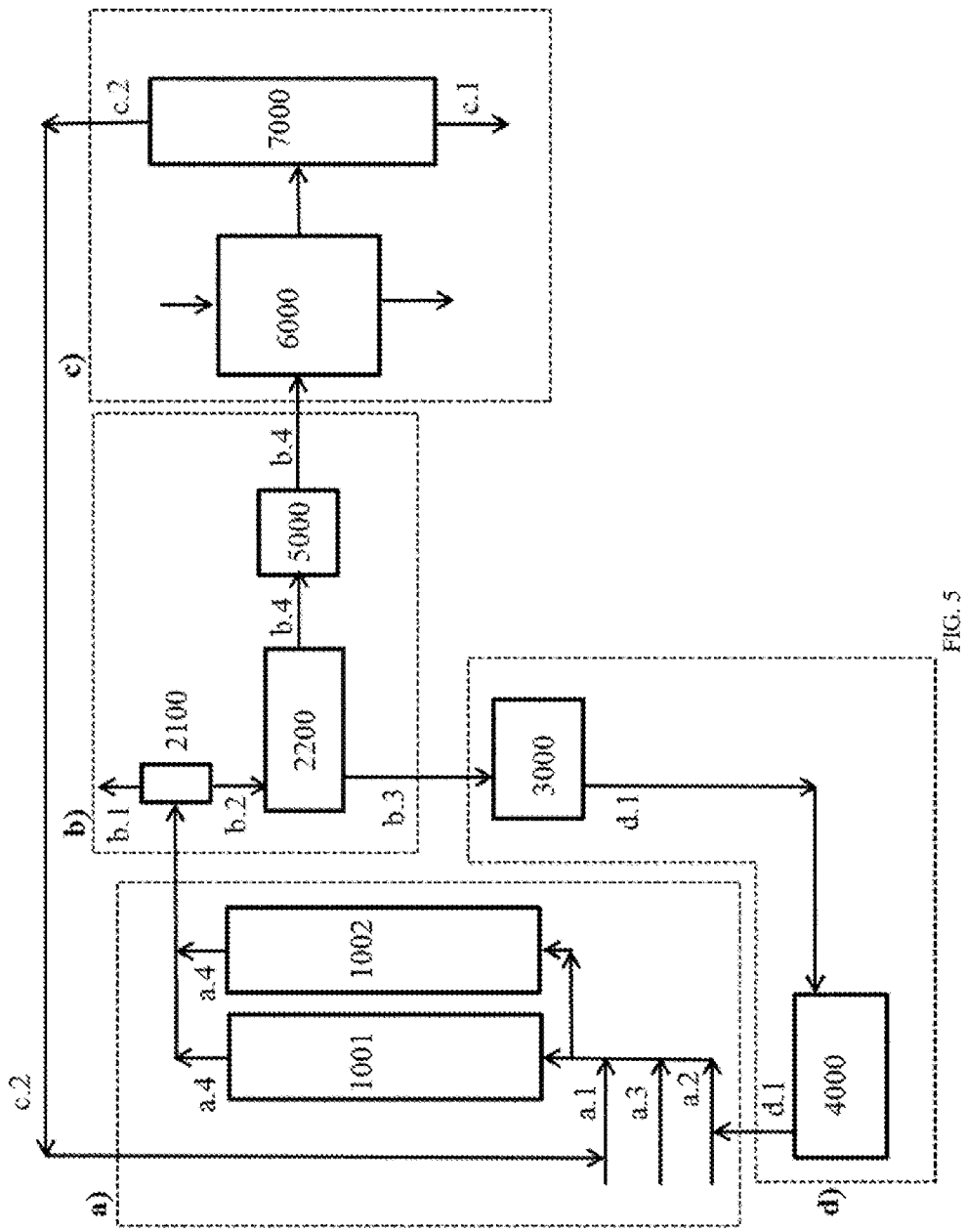
FIG. 5 shows a possible configuration of a production plant according to the invention having two reactors operated in parallel.

Variant (α) is very particularly preferred and is illustrated in FIG. 5 using the example of two reactors 1001 and 1002. Control valves and the like are not illustrated so as not to complicate the drawing. By combining the individual process products (a.4) in a common pipe upstream of the gas separator and hence also upstream of the phase separation apparatus, the phase separation is facilitated since undesired flows in the apparatus such as crossflows and backflows and also swirl formation, which form due to different proportions of the three phases (aqueous, organic, gas) in the incoming reaction solutions, are reduced or eliminated. As discussed above in connection with the discussion of the process according to the invention, in a departure from the arrangement shown in FIG. 5, it may be expedient to divide the stream b.2 back into a plurality of (preferably 2 to 5, particularly preferably 2 to 3) substreams and to feed these to the phase separation apparatus at spatially different locations via a corresponding number of inlet connections. The problems possible when a plurality of inlet connections into the phase separation apparatus are present without prior homogenization (varying throughputs and reaction conditions in the individual lines can in the case of a plurality of entry openings lead to varying and highly differing velocities at the entrances and hence to unknown flow conditions in the phase separation apparatus) can be avoided here.

The procedure according to the invention gives rise at least to the following advantages:

i) As a result of the degassing of the reaction solutions upstream of the phase separation apparatus, velocities and turbulence in the entry region of the phase separation apparatus are reduced, which can increase the separating efficiency.

ii) The phase separation times in the phase separation apparatus are minimized, as a result of which the investment costs for this apparatus become lower, or a production increase in an existing plant becomes easier.

iii) As a result of the improved phase separation, the entrainment of organics into the evaporator of the sulfuric acid concentration is reduced, which reduces energy consumption and avoids problems caused by these organics.

iv) As a result of the improved phase separation, the entrainment of sulfuric acid in the crude nitrobenzene sent for workup is reduced. This brings about savings in feedstocks since the sulfuric acid losses in the workup turn out to be lower.

The wastewater pollution is reduced as less sulfuric acid passes into the wastewater of step c).

v) Flow-stabilizing internals in the phase separation apparatus, which are prone to disruptive soiling and caking, can generally be dispensed with.

vi) Optional homogenization of the reaction solution: As a result of the single-line feed into the phase separation apparatus, the turbulence can be better controlled and optimized compared to a multi-line feed of the reaction solutions with fluctuating process conditions.

The present invention shall be illustrated below by means of examples.

EXAMPLES

The following two examples are intended to make clear the negative influence of the presence of a gas phase on the phase separation (example 1) and also the advantage of an upstream gas separation (example 2). To this end, Computational Fluid Dynamics simulations were performed of the triphasic flow behavior in the phase separation apparatus (apparatus 2200 in FIG. 4). In the examples discussed, three reactors are operated in parallel. For the simulation, it was assumed that the streams exiting the three reactors (process product a.4, here comprising three streams a.4.1, a.4.2, a.4.3) are identical with respect to temperature, mass flow and composition and each contain 250 t/h of aqueous phase (sulfuric acid phase), 14 t/h of organic phase (nitrobenzene phase) and 0.15 t/h of gas phase (mainly benzene) and have a temperature of 130° C. The phase separation apparatus is operated at an absolute pressure (in the gas phase) of approx. 1.1 bar.

Figure 6:
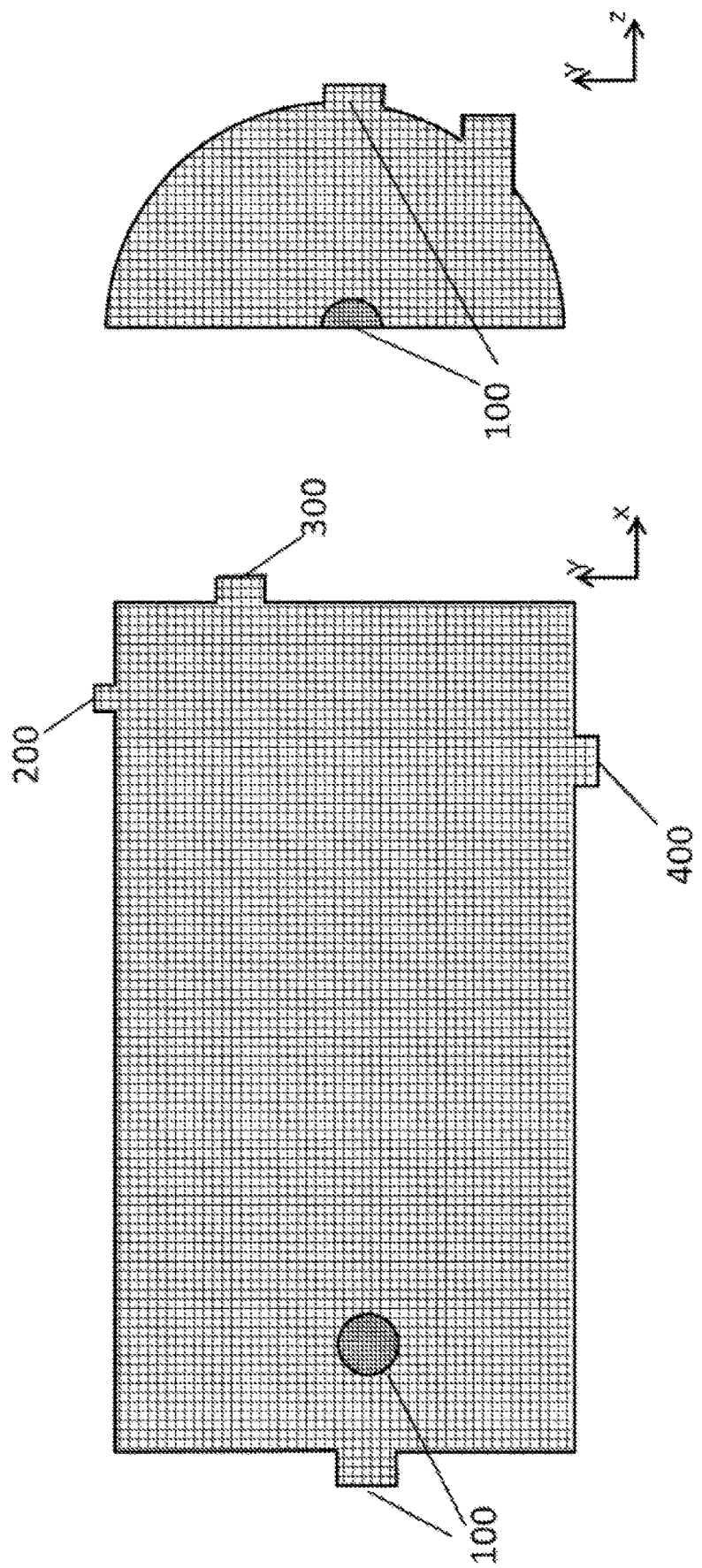
FIG. 6 shows the grid used for the Computational Fluid Dynamics (CFD) calculations of the examples.

FIG. 6 illustrates the employed 3D grid of the phase separation apparatus, with 800 000 computational cells. The following references apply in the drawing:

100: Inlet connection
200: Gas phase exit
300: Organic phase outflow
400: Aqueous phase outflow For the sake of simplicity, the phase separation apparatus has been depicted as a cylinder, without considering curvatures of the lateral covers. Due to the axial symmetry, only half of the phase separation apparatus needs to be modeled. The process products of the three reactors (a.4) flow in via inlet connections on the left-hand side. The outflow of the organic phase (b.4) is situated in the middle on the right-hand side. The outflow of the aqueous phase (b.3) is situated at the lower end. The gas phase (b.1) can be taken off at the top. The triphasic flow was simulated using a Euler-Euler approach, the aqueous phase being described as the continuous phase and the organic phase and the gas phase being described as the disperse phase. The continuity and conservation of momentum equations were solved for all phases in the context of the simulation. The turbulence model used was a k-epsilon model. The equations were solved transiently, the time steps being varied between 0.1 s and 0.001 s.

Since the exact droplet/bubble sizes on entry into the phase separation apparatus or else in the phase separation apparatus itself are not known, a constant droplet/bubble diameter of 1 mm was assumed for both phases. Since droplets and bubbles in reality follow a certain size distribution and breakup and coalescence processes take place in the apparatus, the actual particle sizes and the resulting phase proportions in the apparatus may vary. The objective of the CFD simulation is to qualitatively describe the influence of a gas phase on the flow conditions and ultimately the separating efficiency of the phase separation apparatus.

The examples consider the case without gas separator (example 1) and with gas separator (apparatus 2100, example 2).

Example 1 (Comparative Example)

In comparative example 1, in each case 250 t/h of aqueous phase, 14 t/h of organic phase and 0.15 t/h of gas phases (mainly benzene)—process product (a.4)—flow out of each of the three reactors and into the phase separation apparatus.

Figure 7:
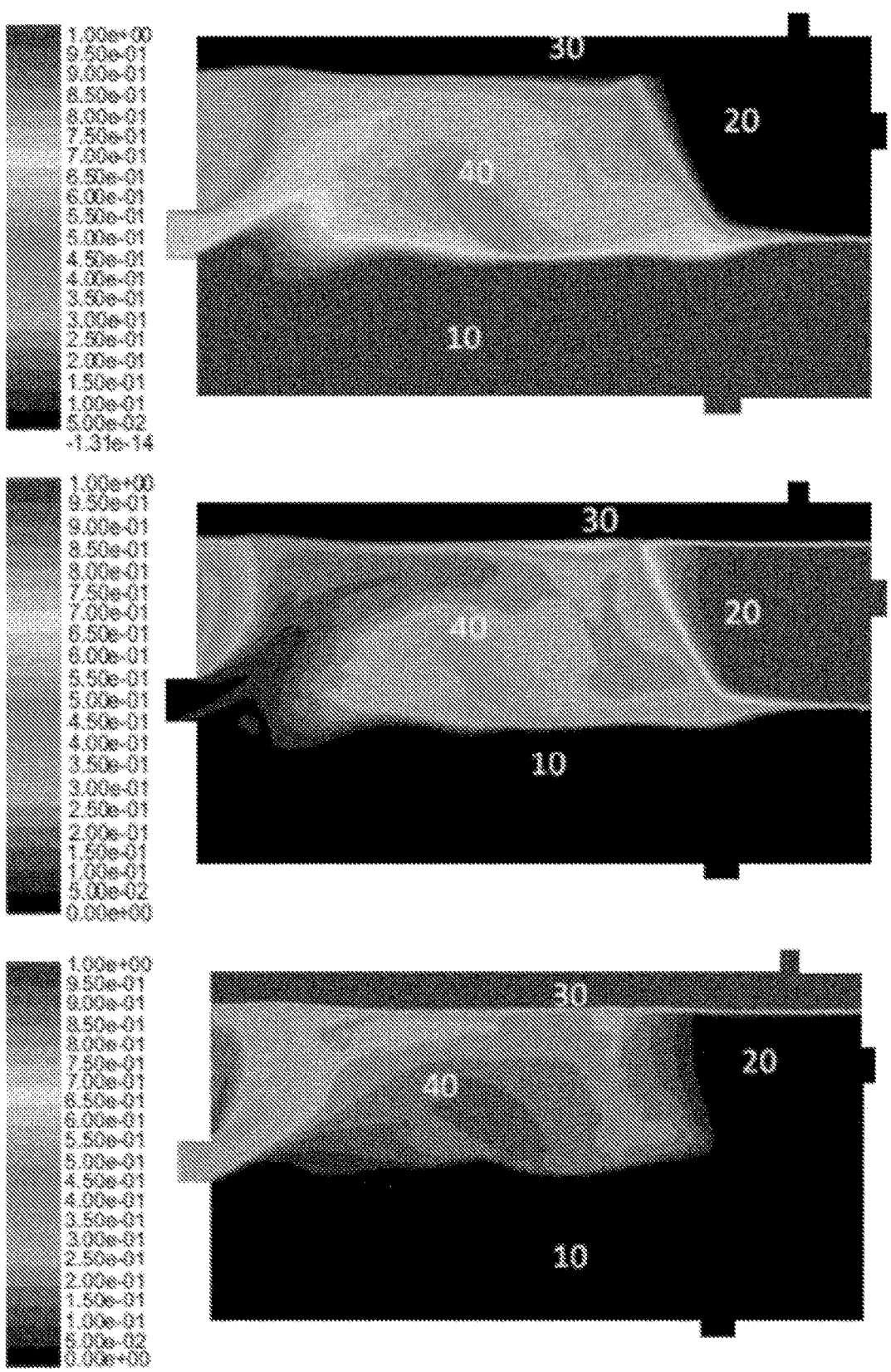
FIG. 7 shows the volume fractions of the three phases (top: aqueous phase, middle: organic phase, bottom: gas phase) in the CFD simulation of example 1 (comparative example; without degassing before entry into the phase separation apparatus)

FIG. 7 illustrates the volume fractions of the three phases in gray scale (top image: volume fractions of aqueous phase, middle image: volume fractions of organic phase, bottom image: volume fractions of gas phase. In the images, the individual phases are also identified with

10: aqueous phase,
20: organic phase,
30: gas phase and
40: disperse phase in which complete mixing has not yet taken place.

The triphasic mixture flows in on the left at the inlet connections in the images. It can be seen in the upper image that, although directly after entry a continuous aqueous phase forms which separates out to the bottom, a large region in which all three phases are present ("disperse" phase) remains in the middle of the phase separation apparatus. This can also be seen in the middle and lower image, where larger volume fractions can also be seen in this region for the organic and gas phase. A continuous organic phase only forms towards the end of the phase separation apparatus (middle image, coherent organic phase on the right-hand side upstream of the outflow of the organic phase). In the lower image, in which the volume fractions of the gas phase are illustrated, it can be seen that the gas phase rises upwards, yet a portion is still entrained far into the apparatus. Due to the low density of the gas phase (approx. 3 kg/m$^3$) there is still a high volume fraction in the region of the entrance and in the middle part of the decanter, despite the low proportion by mass of the gas phase (0.15 t/h out of 250 t/h). The high proportion of gas here also leads in the region of the entrance to higher velocities in the liquid phases (up to 2 m/s) and to swirl in the region of the liquid-liquid phase separation. For such an operation, entrainment of extraneous phase at the individual outlets cannot be excluded, especially if in reality proportions of smaller droplet and gas bubble sizes than the 1 mm diameters simulated here are present, these requiring more time for separation.

In real production, the phase boundary can be observed through a sightglass fitted in the phase separation apparatus. Under the conditions described above, in real operation marked fluctuations in the liquid-liquid phase boundary (±100 mm) are consistently observed on the right-hand side below the exit for the organic phase. In addition, rising gas bubbles are still consistently observed at the sightglass. The simulation is thus confirmed by the observations on the real apparatus.

Example 2 (According to the Invention)

Figure 8:
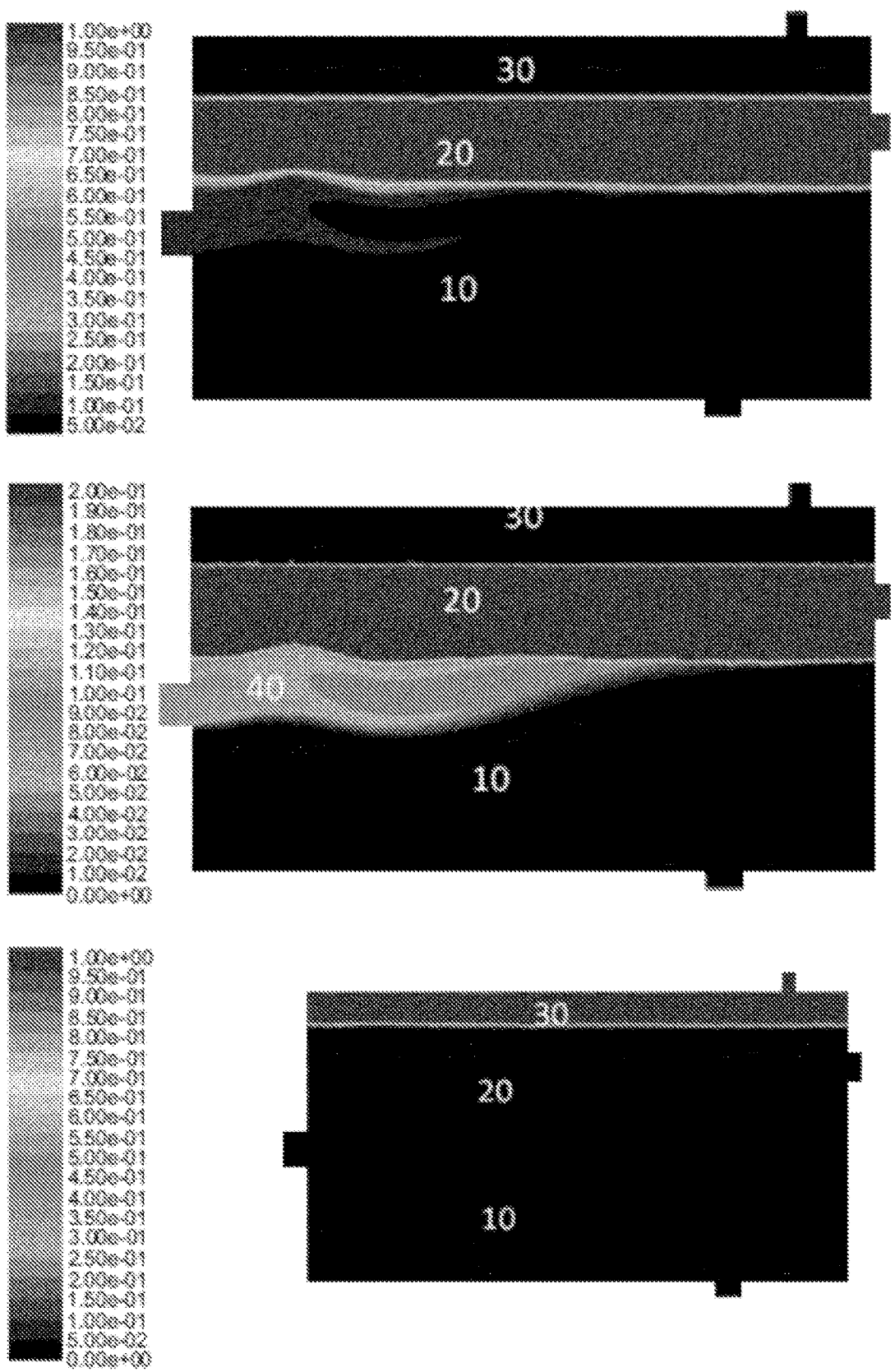
FIG. 8 shows the volume fractions of the three phases (top: aqueous phase, middle: organic phase, bottom: gas phase) in the CFD simulation of example 2 (example according to the invention; with degassing before entry into the phase separation apparatus).

In example 2 according to the invention, the operation of the phase separation apparatus was simulated taking into account upstream degassing. For this purpose, the proportion of the gas phase in each of the three process products (a.4.1, a.4.2, a.4.3) was reduced to 0.012 t/h (the simulation therefore assumes that >90% of the gas phase is removed, which is achievable without problems using conventional degassing apparatuses). In the simulation in each case 250 t/h of aqueous phase and 14 t/h of organic phase continue to flow from each reactor into the phase separation apparatus. The volume fractions of the three phases are in turn illustrated in FIG. 8 (top image: volume fractions of aqueous phase, middle image: volume fractions of organic phase, bottom image: volume fractions of gas phase). In contrast to comparative example 1, it is apparent that a stable continuous aqueous and organic phase forms directly after entry into the phase separation apparatus. Due to the low proportion of gas phase, this no longer interferes with the separation process. The velocities in the region of the entrance are likewise markedly reduced (<1 m/s). Even for small droplet diameters, the flow is stabilized such that a rise and a phase separation are possible. For such an operation, entrainment of extraneous phase at the individual outlets can very substantially be excluded.

The positive effect was also demonstrated in real operation, where after installation of the gas separator the phase boundary in the phase separation apparatus was stabilized and in addition no rising gas bubbles could be seen in the vicinity of the exit.

The invention claimed is:

1. A process for the continuous preparation of nitrobenzene, comprising:
   a) adiabatically reacting a benzene-containing stream in a reactor with sulfuric acid and nitric acid using a, based on nitric acid, stoichiometric excess of benzene, to obtain a process product containing nitrobenzene, benzene and sulfuric acid;
   b) (i) passing the process product containing nitrobenzene, benzene and sulfuric acid into a gas separator in which a gaseous phase comprising benzene and gaseous secondary components is removed from the process product, leaving a liquid phase comprising nitrobenzene and sulfuric acid and depleted of gaseous constituents;
   (ii) passing the liquid phase produced in step b)(i) into a phase separation apparatus in which the liquid phase is subjected to a phase separation, wherein a liquid aqueous, sulfuric acid-comprising phase and a liquid organic, nitrobenzene-comprising phase are withdrawn from the phase separation apparatus; and
   c) working up the liquid organic, nitrobenzene comprising phase to obtain the nitrobenzene.

2. The process as claimed in claim 1, further comprising:
   d) concentrating the liquid aqueous, sulfuric acid-comprising phase by evaporation of water to give a concentrated liquid aqueous phase comprising a higher concentration of sulfuric acid as compared to the liquid aqueous, sulfuric acid-comprising phase, wherein the concentrated liquid aqueous phase is recycled into step a) and used as constituent of the sulfuric acid.

3. The process as claimed in claim 1, in which the workup of the liquid organic, nitrobenzene-comprising phase comprises:
   (i) washing the liquid organic, nitrobenzene-comprising phase and removing unconverted benzene, and
   (ii) using removed benzene as a constituent of the benzene used in step a).

4. The process as claimed in claim 1, in which the stoichiometric excess of benzene based on nitric acid in step a) is set to a value in the range from 2.0% to 40% of theory.

5. The process as claimed in claim 1, in which the temperature in the reactor of step a) is maintained in the range from 98° C. to 140° C.

6. The process as claimed in claim 1, in which step a) is performed in a plurality of reactors operated in parallel and
   ($\alpha$) the process products containing nitrobenzene, benzene and sulfuric acid that are obtained in each of the plurality of reactors are combined prior to performing step b)(i); or
   ($\beta$) the process products containing nitrobenzene, benzene and sulfuric acid that are obtained in each of the plurality of reactors are each passed in step b)(i) into a dedicated gas separator and the liquid phases comprising nitrobenzene and sulfuric acid and depleted of gaseous constituents that are obtained in the gas separators are combined
   ($\beta$)(1) in the phase separation apparatus of step b)(ii) or
   ($\beta$)(2) prior to performing step b)(ii);
   or
   ($\gamma$) the process products containing nitrobenzene, benzene and sulfuric acid that are obtained in each of the plurality of reactors are passed in step b)(i) into a common gas separator without prior combining.

7. The process as claimed in claim 1, in which the gas separator used comprises a gravitational separator or a centrifugal separator.

8. The process as claimed in claim 7, in which the gas separator comprises a gravitational separator.

9. The process as claimed in claim 8, in which the gravitational separator comprises a horizontally or vertically arranged gravitational separator to which the process product containing nitrobenzene, benzene and sulfuric acid
   is fed from the side or from the bottom, wherein the gaseous phase comprising benzene and gaseous secondary components is withdrawn from the gravitational separator as a top stream and the liquid phase comprising nitrobenzene and sulfuric acid and depleted of gaseous constituents is withdrawn from the gravitational separator as a bottom stream at the bottom or from the side, or
   is fed from the top, wherein the gaseous phase comprising benzene and gaseous secondary components is withdrawn from the gravitational separator from the side and the liquid phase comprising nitrobenzene and sulfuric acid and depleted of gaseous constituents is withdrawn from the gravitational separator at the bottom.

10. The process as claimed in claim 7, in which the gas separator comprises a centrifugal separator.

11. The process as claimed in claim 10, in which the centrifugal separator comprises a vertically arranged, cylindrical, conical or cylindrical-conical cyclone through which the process product containing nitrobenzene, benzene and sulfuric acid is guided with the generation of swirl, wherein the gaseous phase comprising benzene and gaseous secondary components is discharged towards the top and the liquid phase comprising nitrobenzene and sulfuric acid and depleted of gaseous constituents is discharged towards the bottom.

12. The process as claimed in claim 1, in which the reactor used in step a) comprises a tubular reactor.

13. A production plant for performing the process for the continuous preparation of nitrobenzene as claimed in claim 1, comprising:
   a) a reactor configured to adiabatically react a benzene-containing stream with sulfuric acid and nitric acid using a, based on nitric acid, stoichiometric excess of benzene;
   b) (i) a gas separator arranged downstream of the reactor, the gas separator being configured to separate the process product from the reactor into a gaseous phase comprising benzene and gaseous secondary components and a liquid phase comprising nitrobenzene and sulfuric acid and depleted of gaseous constituents;
   (ii) a phase separation apparatus arranged downstream of the gas separator, the phase separation apparatus being configured to separate the process product from the gas separator into a liquid aqueous, sulfuric acid-comprising phase and a liquid organic, nitrobenzene-comprising phase; and
   c) an apparatus configured to work up the liquid organic, nitrobenzene-comprising phase from the phase separation apparatus to give the nitrobenzene; and
   d) optionally, devices configured to concentrate the liquid aqueous, sulfuric acid-comprising phase from the phase separation apparatus by evaporation of water and devices configured to recycle the liquid aqueous phase thus obtained comprising a higher concentration of sulfuric acid compared to the liquid aqueous, sulfuric acid-comprising phase into the reactor as a constituent of the sulfuric acid.

14. The production plant as claimed in claim 13, comprising
   a) a plurality of reactors configured to operate in parallel for the adiabatic reaction of a benzene-containing stream with sulfuric acid and nitric acid using a, based on nitric acid, stoichiometric excess of benzene; and
   in a variant ($\alpha$),
   b) (i-0) arranged downstream of the reactors, devices configured to combine the process products containing nitrobenzene, benzene and sulfuric acid that are obtained in the reactors to form a mixed stream and configured to introduce the mixed stream into
   (i) a gas separator, arranged downstream of the devices configured to combine the process products containing nitrobenzene, benzene and sulfuric acid that are obtained in the reactors, the gas separator being configured to separate the mixed stream into a gaseous phase comprising benzene and gaseous secondary components and a liquid phase comprising nitrobenzene and sulfuric acid and depleted of gaseous constituents, and
   (ii) a phase separation apparatus, arranged downstream of the gas separator, the phase separation apparatus being configured to separate the liquid phase comprising nitrobenzene and sulfuric acid and depleted of gaseous constituents into a liquid aqueous, sulfuric acid-comprising phase and a liquid organic, nitrobenzene-comprising phase;
   or, in a variant ($\beta$),
   b) (i) arranged downstream of the reactors, a plurality of gas separators operated in parallel and configured to separate the process product of each reactor into a gaseous phase comprising benzene and gaseous secondary components and a liquid phase comprising nitrobenzene and sulfuric acid and depleted of gaseous constituents, and
   (ii) a phase separation apparatus, arranged downstream of the gas separators, the phase separation apparatus being configured to separate the liquid process product from the plurality of gas separators into a liquid aqueous, sulfuric acid-comprising phase and a liquid organic, nitrobenzene-comprising phase, wherein optionally devices configured to combine the liquid phases comprising nitrobenzene and sulfuric acid and depleted of gaseous constituents that are obtained in the gas separators are arranged between the plurality of gas separators operated in parallel and the phase separation apparatus;
   or, in a variant ($\gamma$),
   b) (i) arranged downstream of the reactors, a gas separator common to all reactors and configured to separate the process products of the reactors into a gaseous phase comprising benzene and gaseous secondary components and a liquid phase comprising nitrobenzene and sulfuric acid and depleted of gaseous constituents, and
   (ii) a phase separation apparatus, arranged downstream of the gas separator, the phase separation apparatus being configured to separate the liquid phase from the gas separator comprising nitrobenzene and sulfuric acid and depleted of gaseous constituents into a liquid aqueous, sulfuric acid-comprising phase and a liquid organic, nitrobenzene-comprising phase.

15. The production plant as claimed in claim 13, wherein the reactor comprises a tubular reactor.

16. The production plant as claimed in claim 14, wherein the plurality of reactors comprise a tubular reactor.

* * * * *